United States Patent [19]

Besnier

[11] Patent Number: 5,504,343

[45] Date of Patent: Apr. 2, 1996

[54] DEVICE FOR STORING CYLINDRICAL OBJECTS WITH FAST CHARGING AND DISCHARGING

[75] Inventor: Joseph Besnier, Acqueville, France

[73] Assignee: Compagnie Generale Des Matieres Nucleaires, Velizy-Villacoublay, France

[21] Appl. No.: 286,699

[22] Filed: Aug. 5, 1994

[30] Foreign Application Priority Data

Aug. 20, 1993 [FR] France .................................. 93 10149

[51] Int. Cl.⁶ .............................................. G01N 35/10
[52] U.S. Cl. ........................ 250/507.1; 422/65; 422/104; 376/272; 414/146
[58] Field of Search ............................ 250/507.1, 505.1, 250/506.1, 515.1; 422/63, 65, 102, 104; 376/272, 264; 141/98, 311 R, 351; 221/198, 197, 222, 226–231; 414/138.8, 138.9, 146

[56] References Cited

U.S. PATENT DOCUMENTS

| 4,168,599 | 9/1979 | King ...................................... 414/146 |
| 4,595,562 | 6/1986 | Liston et al. ............................. 422/65 |
| 4,680,159 | 7/1987 | Lahr et al. ........................... 250/507.1 |

Primary Examiner—Jack I. Berman
Assistant Examiner—Kiet T. Nguyen
Attorney, Agent, or Firm—Pearne, Gordon, McCoy & Granger

[57] ABSTRACT

A device for storing cylindrical objects, such as small containers (14) containing radioactive material samples, includes one or more superimposed rotary racks (30, 30'). Each of the racks has circumferentially distributed cavities (32, 32') in which the objects are received. The cavities are radially outwardly open with respect to the vertical rotation axis of the racks (30, 30'). Moreover, their axis is inclined so as to intersect the rotation axis above the cavity. Thus, an accidental escape of the objects is prevented.

10 Claims, 2 Drawing Sheets

DEVICE FOR STORING CYLINDRICAL OBJECTS WITH FAST CHARGING AND DISCHARGING

FIELD OF THE INVENTION

The invention relates to a device for storing objects having a substantially cylindrical configuration in a restricted volume and in such a way that said objects can be rapidly charged and discharged.

BACKGROUND OF THE INVENTION

The storage device according to the invention can be used in numerous industrial fields, whenever an intermediate storage is required in a relatively reduced volume within an automated installation.

A preferred application of the invention relates to the storage of small containers or jugs containing chemical products such as radioactive products, prior to the analysis thereof, within a tight cell in which analysis is to take place. More specifically, the preferred application relates to an automated installation like that described in FR-A-2 675 582, in which liquid samples are sampled in an automated manner at different points of a production or processing chain, and introduced into containers and automatically transferred to analysis boxes or cases by pneumatic transfer circuits.

In such an installation, the containers containing the samples to be analyzed drop directly into the bottom of the analysis boxes, which leads to a certain number of problems which will now be described.

A first problem relates to the identification of the containers, which takes place by reading a code carried by each container. In view of the fact that all the containers are loosely arranged in the bottom of the analysis box, the operator has to seek, with the aid of grippers, the particular container of interest to him. This fastidious operation is further complicated by optical deformations of the shielding window through which the operator reads the codes carried by the containers.

Another problem results from the fact that during their transportation and when they pass into the analysis box, the containers are located in a receptacle carrying the aforementioned identification code. In order to carry out the analysis, the operator must successively remove the container from the receptacle and then open the container, which constitutes an error source. In order to avoid such errors, the operator usually places the containers in a rack having holes after extracting the containers from their receptacles and notes the codes of the samples corresponding to said holes on paper stuck to the exterior of the box. However, this makes the procedure more difficult, particularly when there is a team change.

Another problem is due to the outflow of analytical liquids, which normally takes place through the bottom of the box to a syphon system. As soon as the containers drop in the analysis box, they are externally contaminated by these analytical liquids. At the time of the opening of the containers, external contamination can bring about a pollution of the interior of the container, which falsifies the analysis result.

In an installation like that described in FR-A-2 675 582, certain of the containers entering a given analysis box have to be redispatched to other analysis boxes without being opened. The external contamination of the containers due to their contact with the analytical liquids flowing in the bottom of the analysis box then pollutes the pneumatic transfer systems, which become of an irradiative nature with respect to personnel. To obviate this disadvantage, it is consequently necessary, within the analysis box, to carry out a transfer of the samples contained in the externally contaminated containers into uncontaminated containers, For example, for this purpose use is made of a transfer device, as described in FR-A-2 679 035. However, although the use of such a transfer device makes it possible to protect personnel from irradiation, it leads to the creation of supplementary solid waste in the form of the externally irradiated containers.

In numerous industrial sectors, the problem of the provisional storage of generally cylindrical objects is solved by having recourse to storage devices incorporating a vertically axed, rotary rack having on its periphery one or more rows of cylindrical cavities or recesses, whose axes are also vertical. The charging or loading and the discharging or unloading of the objects takes place vertically, generally from the top of the cavities. In certain cases, the objects can be discharged via the bottom of the cavities.

This generally satisfactory configuration suffers from the disadvantage of imposing on the external diameter of the rack dimensions which can be excessive when the number of cavities is increased. This problem becomes particularly delicate when it is intended to use such a storage device within an analysis box having to contain a certain number of other devices in a restricted volume.

The invention specifically relates to a storage device making it possible to store a relatively large number of substantially cylindrical objects in a limited diameter, so as to permit use in an analysis box of an installation like that described in FR-A-2 675 582, while solving the aforementioned problems caused by the dropping of the containers into the bottom of said box.

SUMMARY OF THE INVENTION

According to the present invention a device for the storage of objects is provided, the device having a substantially cylindrical configuration comprising at least one storage rack which can be turned around a vertical axis and provided with cavities able to receive the objects circumferentially distributed around the vertical axis and means for controlling the rotation of the rack around the vertical axis, wherein the cavities are open radially to the outside to permit radial introduction and extraction of the objects and each cavity has an axis inclined so as to intersect the vertical axis of the rack above the latter.

As a result of this arrangement, charging and discharging of the cavities take place radially, which makes it possible to envisage the superimposing of several storage racks in a restricted volume. The accidental escape of objects is prevented by the inclination of the axes of the cavities.

Advantageously, an ejecting member is placed in each cavity and has an active part which can perform a substantially radial movement with respect to the vertical axis of the rack between a retracted position and an ejection position.

The ejecting member can, in particular, be constituted by a rocking lever mounted so as to pivot on a horizontal shaft placed in the top of the cavity and oriented perpendicular to a radial direction with respect to the vertical axis of the rack. The active part is then constituted by a first branch of the lever normally oriented downwards parallel to the axis of the cavity and along the wall of the cavity closest to the vertical axis of the rack, from the pivot pin of the lever.

The rocking lever also has a second branch normally oriented radially to the vertical axis of the rack and in a substantially horizontal direction. Ejection means exert a downward thrust or pressure on the second lever branch.

The ejection means advantageously incorporate a jack mounted on a support and a vertical thrust or pressure rod able to move parallel to itself during an actuation of the jack. A bottom end of the thrust rod is placed above the second branch of the rocking lever associated with a cavity positioned to the right of an ejection station of the device.

The device advantageously comprises two storage racks positioned coaxially above one another. The cavities of the two racks are then angularly displaced about their vertical axis and the ejection means incorporate, for each cavity of the lower rack, a vertical rod section mounted so as to slide between two cavities of the upper rack and whose lower end is flush with the second branch of the rocking lever of said cavity of the lower rack. The ejection means also have means for returning the vertical rod section to an upper position.

Advantageously, means are also provided for moving the storage racks parallel to their vertical axis, so as to permit an introduction and extraction of the objects at a constant level.

BRIEF DESCRIPTION OF THE DRAWINGS

The invention is described in greater detail hereinafter relative to a non-limitative embodiment and the attached drawings, wherein show.

DETAILED DESCRIPTION OF THE PREFERRED EMBODIMENTS

Figure 1:
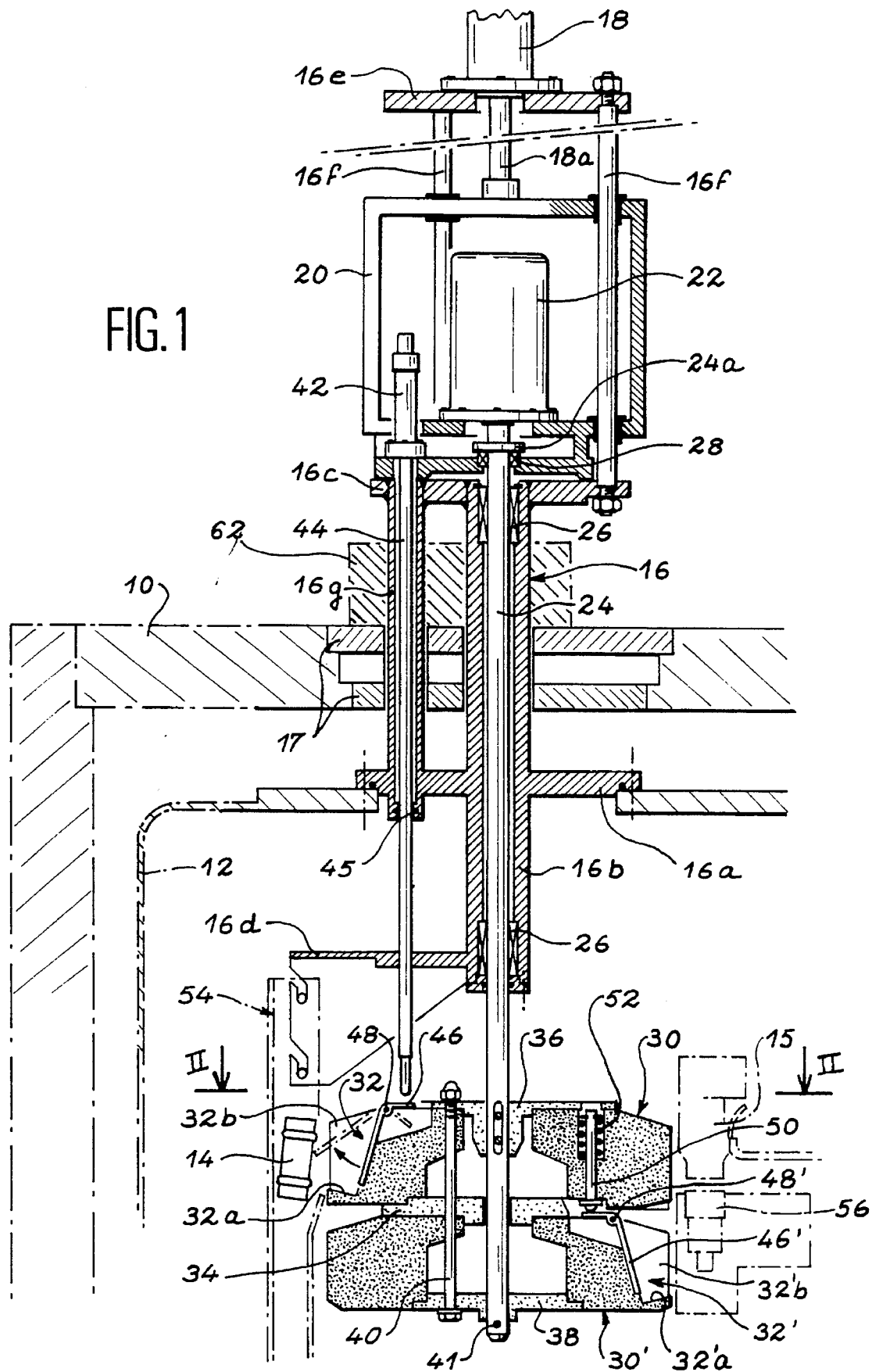
FIG. 1 In vertical section a storage device according to the invention placed in an analysis box.

FIG. 1 shows part of the wall 10 of a tight confinement cell of an analysis box usable in the nuclear industry. The wall 10 is internally duplicated by a metal skin 12. The analysis box partly shown in FIG. 1 receives small containers or jugs 14 containing a sample of a radioactive product, generally in the liquid state and whose analysis is to be carried out. The containers 14 penetrate the analysis box, e.g. by a not shown, vertical tube, which issues into a receptacle 15, (FIG. 2) like that described in FR-A-2 675 582.

According to the invention, the receptacle 15 is placed in the vicinity of the storage racks 30, 30' of a storage device associated with the analysis box. Whereas the storage racks 30, 30' are located within the analysis box, the different control members (actuators) and checking members (sensors) are located outside the same. This arrangement makes it possible to utilize industrial sensors and actuators and not specific laboratory equipments. Thus, maintenance can be carried out by the standard workshop teams.

Moreover, the positioning of the actuators and sensors outside the analysis box makes it possible to limit the costs linked with the scrapping of said equipments in the case of a failure or malfunction.

A storage device illustrated in FIG. 1 comprises a support 16 traversing the upper horizontal parts of the wall 10 and the metal skin 12 and is fixed to the metal skin. More specifically, the support 16 comprises a lower, horizontal disk 16a able to be fixed by screws (not shown) to the metal skin 12 about a circular opening formed in the horizontal part of the skin. The fitting of the disk 16a takes place through a circular opening formed in the horizontal part of the wall 10, the circular opening normally being closed by a two-part plug 17.

In accordance with the axis of the disk 16a, the support 16 also has a vertical tube 16b, whose top end is fixed to the center of an intermediate, horizontal disk 16c placed outside the analysis box. At its lower end located in the analysis box, the vertical tube 16b supports a suspension arm 16d.

Above the intermediate, horizontal disk 16c, the support 16 has an upper, horizontal disk 16e fixed to the disk 16c by vertical guidance columns 16f.

On its upper face, the upper, horizontal disk 16e supports a jack 18, e.g. of the pneumatic type. The rod 18a of the jack 18 projects vertically downwards through the horizontal disk 16e and carries at its bottom end a mobile support 20 on which is mounted a stepping motor 22. More specifically, the mobile support 20 carrying the stepping motor 22 is slidingly received on the vertical guidance column 16f, so as to be able to move vertically between a top position and a bottom position during the actuation of the jack 18.

The stepping motor 22 drives a vertical control shaft 24 in rotary manner, the control being mounted in the tube 16b of the support 16 so as to be able to move freely in rotation and translation therein. For this purpose, the control shaft 24 is supported at each of the ends of the tube 16b by ball holders 26 equipped with packings. In addition, the socket or holder 26 located at the lower end of the tube 16b is equipped with a not shown scraping joint.

In order to take up the forces due to the load suspended at the lower end of the control shaft 24, the latter bears by a collar 24a on the mobile support 20 by means of a thrust ball bearing 28.

The lower end of the control shaft 24, which projects downwards beyond the bottom end of the tube 16b, supports two superimposed storage racks 30, 30' forming the active part of the storage device within the analysis box. The upper rack 30, like the lower rack 30', are constituted by two horizontal, circular plates, which are fixed in accordance with their common vertical axis to the lower end of the control shaft 24, so as to be able to rotate about the vertical axis of the shaft when the stepping motor 22 is operated.

The thickness of each of the plates forming the racks 30, 30' slightly exceeds the length of each of the containers 14, so that the containers can be received in the cavities 32, 32' regularly distributed over the circumference of each of the racks 30, 30'. Thus, and as illustrated in exemplified manner in FIG. 2, each of the racks 30, 30' can have ten (or multiples of five) cavities 32, 32' of identical dimensions on its periphery.

Each of the cavities 32, 32' is open towards the top and radially towards the outside with respect to the vertical axis of the control shaft 24. Each cavity 32, 32' has an axis inclined according to the same given angle, e.g. by approximately 30°, so as to intersect the common vertical axis of the racks 30, 30' at a location above the latter racks. Each cavity 32, 32' has a planar bottom 32a, 32'a perpendicular to the axis of the considered cavity, as well as a side wall 32b, 32'b having a U-shaped cross-section open radially towards the outside with respect to the vertical axis of the racks.

The characteristics described hereinbefore make it possible to introduce the containers 14 radially into the cavities 32, 32' and extract them therefrom in the same way. Thus, it is possible in the restricted overall dimensions corresponding to the superimposing of the racks 30 and 30', to store a relatively large number of jugs 14, e.g. twenty in the present case. The inclined character of the axis of each of the cavities 32, 32' makes it possible to avoid any risk of accidental escape of the containers 14 during a rotation of the storage racks 30, 30' controlled by the stepping motor 22.

In the embodiment illustrated in FIG. 1, the storage racks 30, 30' are, e.g. made from a recessed plastics material, so that the weight suspended on the vertical control shaft 24 is as small as possible.

The upper rack 30 rests on the lower rack 30' by means of a flange 34 and the thus formed assembly is placed between an upper flange 36 and a lower flange 38 and assembled by means of vertical bolts 40. This assembly is integral in rotation with the vertical control shaft 24, e.g. by means of a remotely controllable pin 41 traversing the shaft below the lower flange 38.

The assembly of the upper storage rack 30 and the lower storage rack 30' by means of bolts 40 takes place in such a way that there is a displacement of a half pitch between the cavities 32 of the rack 30 and the cavities 32' of the rack 30'. In other words, each of the cavities 32 of the upper storage rack 30 is, in plan view, between two cavities 32' of the lower storage rack 30' equidistant of each of the said cavities. This arrangement makes it possible to control, with the aid of a single jack, the ejection of containers 14 placed in the receptacles 32 of the upper storage rack 30 and also the ejection of containers 14 placed in the receptacles 32' of the lower storage rack 30'.

As illustrated in FIG. 1, the ejection means used for controlling the ejection of the containers 14 comprise a single jack 42, e.g. of the pneumatic type, mounted on the mobile support 20. When actuated, the jack 42 controls the displacement along its axis, towards the bottom or top, of a vertical thrust rod 44, whose axis is displaced with respect to the vertical axis of the control shaft 24. More specifically, the thrust rod 44 projects downwards and penetrates the analysis box across a sleeve 16g, whose ends are fixed to the lower 16a and intermediate 16c disks of the support 16 and which traverses the plug 17.

A sealing system such as one or more scraping joints 45 is mounted in the lower end of the sleeve 16g, so as to be in tight contact with the thrust rod 44.

Within the analysis box, the thrust rod 44 is guided by the suspension arm 16d and its vertical axis is located in a fixed angular location permanently intersecting the axis of one of the cavities 32 of the upper storage rack 30 or one of the cavities 32' of the lower storage rack 30'.

An ejecting member constituted by a rocking lever 46, 46' is installed in each of the cavities 32, 32' of the racks 30, 30' respectively. Each of the rocking levers 46, 46' is mounted on the rack 30, 30' corresponding thereto by a horizontal pivot pin 48, 48'. More specifically, each lever 46, 46' is shaped like a V, whose apex pivots about the pin 48, 48', said pin being placed at the top of the cavity 32, 32' corresponding thereto and oriented perpendicular to a radial direction with respect to the vertical axis common to the racks 30, 30'.

Each of the rocking levers 46, 46' has an active part constituted by a relatively long branch normally resting by gravity in the bottom of the U possessed in cross-section by the side wall 32b, 32'b of the corresponding cavity 32, 32'. This branch is then oriented downwards from the pivot pin 48, 48' parallel to the axis of the cavity and along the wall of the latter closest to the vertical axis of the racks 30, 30'.

Each of the rocking levers 46, 46' also comprises a second, relatively shorter branch normally oriented radially towards the vertical axis common to the racks 30, 30' and in a substantially horizontal direction from the pivot pin 48, 48'.

As illustrated in FIG. 1, when one of the cavities 32 of the upper storage rack 30 has its axis intersecting the thrust rod 44, the lower end of the thrust rod is positioned immediately above the end of the second branch located in the corresponding cavity 32, when the thrust rod 44 is in the top position. Consequently the descent of the thrust rod 44 controlled by the jack 42 has the effect of pivoting the lever 46 in the clockwise direction in the case of FIG. 1, as illustrated in mixed line form therein. It should be noted that this pivoting is rendered possible by the fact that the rack 30 is recessed below the horizontal branch of each of the rocking levers 46. This pivoting has the consequence of radially moving towards the outside the branch forming the active part of the corresponding lever 46, so that the container 14 previously located in said cavity is expelled radially to the outside.

When the axis of the thrust rod 44 intersects the axis of a cavity 32' of the lower rack 30', means must be provided for ensuring that the descent of the rod 44 is transmitted to the rocking lever 46' associated with the cavity. To this end a section of a vertical rod 50 is mounted so as to slide in the upper storage rack 30 above the end of the upper, horizontal branch of each of the rocking levers 46' mounted on the lower storage rack 30'. A return spring 52 is interposed between each of the vertical rod sections 50 and the upper storage rack 30, so as to maintain the sections 50 normally in a top position, as illustrated in FIG. 1. In this position, the lower end of each of the rod sections 50 is flush with the horizontal, upper branch of the rocking lever 46' corresponding thereto. The rocking levers 46' then occupy their retracted position permitting the charging of a container 14 into the corresponding cavity 32'. Moreover, the upper end of each of the rod sections 50 is then at a level slightly below that of the bottom end of the thrust rod 44.

When the stepwise rotation of the racks 30, 30' controlled by the motor 22 brings the axis of one of the cavities 32' into such a position as to intersect the axis of the thrust rod 44, the vertical rod section 50 above the cavity 32' is then in the extension of the bottom end of the rod 44. Consequently, when a downward displacement of the rod 44 is controlled by the jack 42, the vertical rod section 50 is forced downwards in opposition to the spring 52, which has the effect of rocking the lever 46' about its pin 48'. If there is a jug 14 in the corresponding cavity 32', it is discharged radially to the outside.

Figure 2:
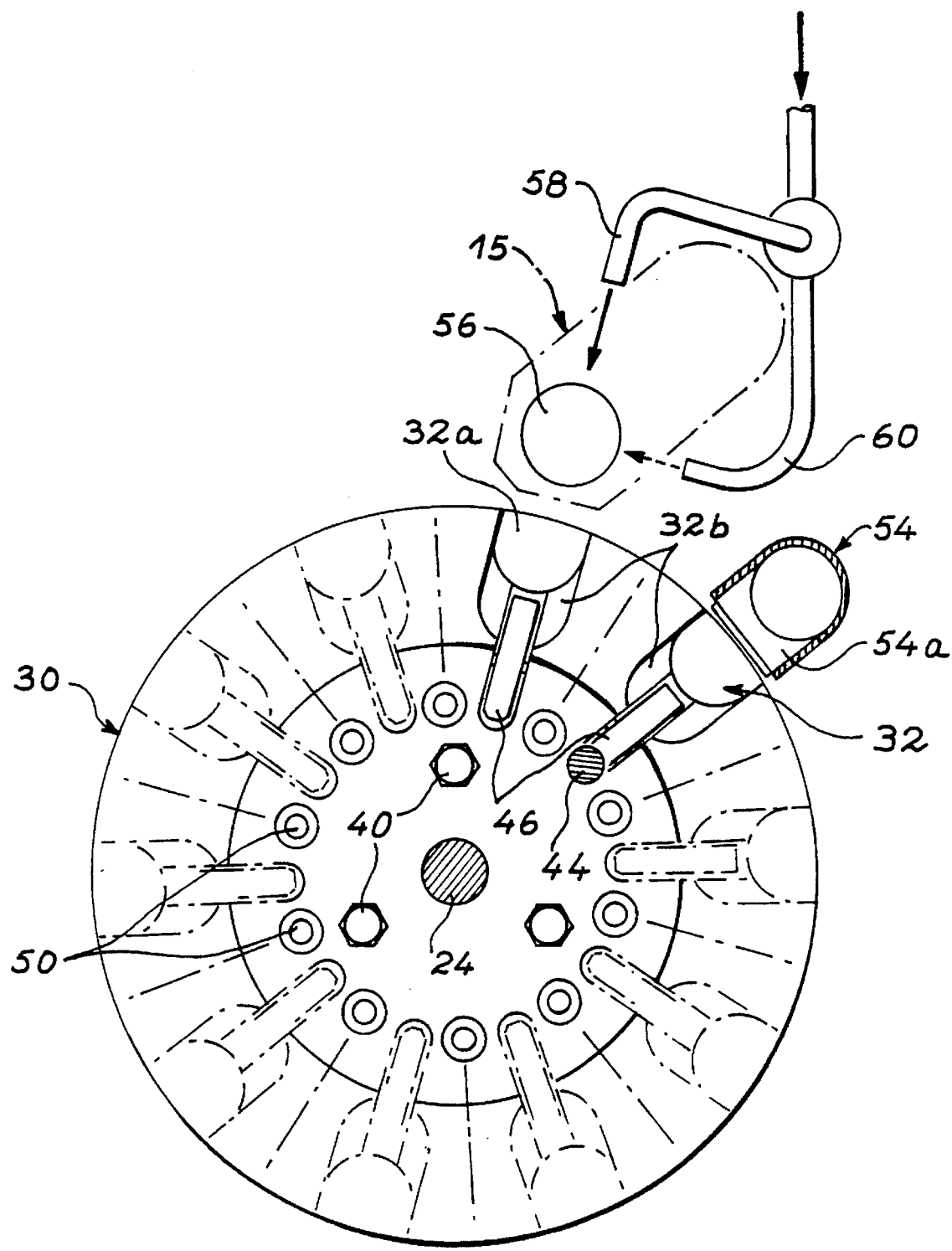
FIG. 2 A diagrammatic sectional view along line II—II of FIG. 1 illustrating the charging station and the ejection station of the device.

In the embodiment according to FIGS. 1 and 2, the ejection station of the containers 14 is materialized by a vertical spout 54 located in the radial plane passing through the axes of the control shaft 24 and the thrust rod 44. The spout 54 is supported by the suspension arm 16d of the fixed support 16 and has a window 54a (FIG. 2) open towards the axis of the storage racks 30, 30'. More specifically, the window 54a is level with the upper storage rack 30 when the two racks are in the bottom position illustrated in FIG. 1 or facing the lower storage rack 30' when the two racks are in the top position. The control of the vertical displacement of the racks 30, 30' between these two positions is brought about by the jack 18.

The charging station for the storage racks 30, 30' is at the same level as the window 54a in the spout 54. It is materialized by the receptacle 15 and by a member 56 which is struck by gravity by the containers 14. This charging station also has a compressed air injector (FIG. 2) able to discharge a compressed air jet making it possible to propel radially towards the cavity 32 or 32' positioned facing the member 56 the jug which is placed on the member 56. As illustrated in FIG. 2, a second compressed air ejector 60 can be provided in order to eject to another, not illustrated device the containers whose storage is not desired.

It should be noted that the compressed air injector used for charging the storage racks has a very limited cost and overall dimensions, unlike a mechanical member whose use would be difficult or even impossible and would slow down the flow rate.

The operation of the device according to the invention will now be described relative to FIGS. 1 and 2. When a container 14 enters the analysis box, it drops onto the member 56. If the container is to be stored and if the cavity 32 or 32' facing the ejector 58 is not free, a rotation of the racks 30, 30' is controlled with the aid of the stepping motor 22, optionally combined with a rise or fall of the racks 30, 30' controlled by the jack 18 in order to bring an empty cavity 32 or 32' facing the container.

The container 14 is then introduced into the corresponding cavity by a compressed air jet produced by the injector 58. As soon as it enters the cavity 32 or 32', the container 14 is automatically placed by gravity in such a way that its axis coincides with the inclined axis of the corresponding cavity. Thus, any subsequent rotation of the racks 30, 30' will not lead to an accidental ejection of the containers supported by these racks.

Moreover, when it is wished to recover one of the containers stored in the racks 30 and 30', the corresponding container is brought facing the window formed in the spout 54 either by a rotation of the racks controlled by the stepping motor 22, or by a rotation controlled by said motor combined with a vertical displacement of the racks controlled by the jack 18. The ejection of the container 14 is then controlled with the aid of the jack 42, whose actuation has the effect of lowering the thrust rod 44.

When the container which it is wished to recover is located in one of the cavities 32 of the upper storage rack 30, the thrust rod 44 controls directly the tilting of the corresponding lever 46, so as to eject the container into the spout 54 in the manner illustrated in FIG. 1.

When the container 14 which it is wished to recover is located in the lower rack 30', the pivoting of the rocking lever 46 associated with the cavity 32' in which the container is located is transmitted from the rod 44 to the lever 46' by means of the rod section 50 located above the lever 46' in question.

The aforementioned description shows that the storage device according to the invention makes it possible to store a relatively large number of containers in a reduced volume. Moreover, the presence of said device in an analysis box makes it possible to avoid the dropping of containers into the bottom of the box and the disadvantages resulting therefrom.

Obviously, the invention is not limited to the embodiment and the application described hereinbefore. Thus, the storage device according to the invention can be used for storing objects with a cylindrical configuration other than these containers and in fields varying significantly from the nuclear field. Moreover, the number of storage containers is not limited to two and the number of cavities formed in each rack can exceed or drop below 10. For simplifying the checking/control performed by the stepping motors, the number of cavities is preferably a multiple of five. In the case where there are more than two superimposed racks, their angular displacement is below a half pitch between two successive cavities of a same rack and rod sections are located in all the racks, with the exception of the bottom rack, in order to transmit to the rocking levers the descent movement of the thrust rod.

Finally, as illustrated at 62 in FIG. 1, an additional biological protection can be placed on the upper wall 10 of the cell between the plug 17 and the disk 16c. This biological protection 62 ensures the protection of personnel when working on the actuating means (jacks 18, 42, stepping motor 22) and the not shown sensors associated therewith.

I claim:

1. Device for the storage of objects having a substantially cylindrical configuration comprising at least one storage rack which is turned around a vertical axis and provided with cavities able to receive the objects circumferentially distributed around said vertical axis and means for controlling rotation of the rack around said vertical axis, wherein the cavities are open radially to the outside, so as to permit radial introduction and extraction of the objects and each cavity has an axis inclined so as to intersect the vertical axis of the rack at a location relatively above the rack.

2. Device according to claim 1, further comprising an ejecting member placed in each cavity and having an active part which is given a substantially radial movement with respect to the vertical axis of the rack between a retracted position and an ejection position.

3. Device according to claim 2, wherein the ejecting member is a rocking lever mounted on a horizontal pivot pin placed at the top of the cavity and oriented perpendicular to a radial direction with respect to the vertical axis of the rack, said active part being constituted by a first branch of the lever normally oriented towards the bottom, upstream of the axis of the cavity and along the wall of each cavity closest to the pivot pin of the lever.

4. Device according to claim 3, wherein the rocking lever has a second branch normally oriented radially towards the vertical axis of the rack and in a substantially horizontal direction, further comprising ejection means for exerting a downward thrust on the second lever branch.

5. Device according to claim 4, wherein the ejection means comprises a jack mounted on a support and a vertical thrust rod able to move parallel to itself during a jack actuation, a bottom end of the thrust rod being placed above the second branch of the rocking lever of each cavity located to the right of an ejection station of the device.

6. Device according to claim 5, wherein at least two storage racks are arranged coaxially in superimposed manner.

7. Device according to claim 6, wherein the cavities of the two racks are angularly displaced about their vertical axis, the ejection means having, for each cavity of the lower rack, a vertical rod section mounted in sliding manner between two cavities of the upper rack and whose lower end is flush with the second branch of the rocking lever of said cavity of the lower rack and means for returning the vertical rod section to a top position.

8. Device according to claim 6, further comprising means for displacing the storage racks parallel to their vertical axis in order to permit introduction and extraction of the objects at a constant level.

9. Device according to claim 8, wherein said objects are radioactive objects, the storage rack being placed within a confinement cell, said means for controlling rotation of the rack comprising a motor and said means for displacing the storage racks comprising a second jack, the motor and the second jack being positioned outside said cell, said device further comprising an additional biological protection placed on the wall of the cell facing said motor and said jacks.

10. Device according to claim 1, further comprising a charging station of the storage rack including a compressed air injector.

* * * * *

UNITED STATES PATENT AND TRADEMARK OFFICE
CERTIFICATE OF CORRECTION

PATENT NO. : 5,504,343

DATED : April 2, 1996

INVENTOR(S) : Besnier

Page 1 of 2

It is certified that error appears in the above-indentified patent and that said Letters Patent is hereby corrected as shown below:

On the title page: Item [54], under References Cited, the following references should also be included:

Under U.S. Patent Documents:

--3,504,376   12/1966   Bednar et al............356/246
  3,751,985   8/1973    Knedel et al............73/423A
  4,634,575   1/1987    Kawakami et al..........422/63
  4,656,007   4/1987    Douchy et al............422/64--

Under Foreign Patent Documents:

--1319542   1/1963    French Patent Office
  83/00393   02/1983   WO-PCT Publication (U.S.)
  180494     5/1986    European Patent Office--.

Column 3, line 49, delete ", (FIG. 2)" and insert --(FIG. 2),--.

UNITED STATES PATENT AND TRADEMARK OFFICE
CERTIFICATE OF CORRECTION

PATENT NO. : 5,504,343

DATED : April 2, 1996

INVENTOR(S) : Besnier

It is certified that error appears in the above-indentified patent and that said Letters Patent is hereby corrected as shown below:

Column 4, line 26, after "control" insert --shaft--, and line 60, delete "latter".

Signed and Sealed this

Fifteenth Day of October, 1996

Attest:

BRUCE LEHMAN

*Attesting Officer*     *Commissioner of Patents and Trademarks*